(12) United States Patent
Chen et al.

(10) Patent No.: US 11,576,851 B2
(45) Date of Patent: Feb. 14, 2023

(54) COMPOSITION OF PICKERING EMULSION

(71) Applicant: L'OREAL, Paris (FR)

(72) Inventors: Huiqin Chen, Shanghai (CN); Xiaomin Weng, Shanghai (CN)

(73) Assignee: L'OREAL, Paris (FR)

( * ) Notice: Subject to any disclaimer, the term of this patent is extended or adjusted under 35 U.S.C. 154(b) by 461 days.

(21) Appl. No.: 16/316,068

(22) PCT Filed: Jul. 12, 2016

(86) PCT No.: PCT/CN2016/089788
§ 371 (c)(1),
(2) Date: Jan. 8, 2019

(87) PCT Pub. No.: WO2018/010094
PCT Pub. Date: Jan. 18, 2018

(65) Prior Publication Data
US 2021/0169768 A1 Jun. 10, 2021

(51) Int. Cl.
| | | |
|---|---|---|
| *A61K 8/73* | (2006.01) | |
| *A61K 8/06* | (2006.01) | |
| *A61K 8/19* | (2006.01) | |
| *A61K 8/24* | (2006.01) | |
| *A61K 8/25* | (2006.01) | |
| *A61K 8/26* | (2006.01) | |
| *A61K 8/28* | (2006.01) | |
| *A61K 8/29* | (2006.01) | |
| *A61K 8/34* | (2006.01) | |
| *A61K 8/36* | (2006.01) | |
| *A61K 8/37* | (2006.01) | |
| *A61K 8/39* | (2006.01) | |
| *A61K 8/46* | (2006.01) | |
| *A61K 8/81* | (2006.01) | |
| *A61K 8/86* | (2006.01) | |
| *A61K 8/88* | (2006.01) | |
| *A61K 8/891* | (2006.01) | |
| *A61K 8/90* | (2006.01) | |
| *A61Q 1/02* | (2006.01) | |
| *A61Q 1/04* | (2006.01) | |
| *A61Q 19/00* | (2006.01) | |

(52) U.S. Cl.
CPC ............... *A61K 8/732* (2013.01); *A61K 8/06* (2013.01); *A61K 8/062* (2013.01); *A61K 8/19* (2013.01); *A61K 8/24* (2013.01); *A61K 8/25* (2013.01); *A61K 8/26* (2013.01); *A61K 8/28* (2013.01); *A61K 8/29* (2013.01); *A61K 8/345* (2013.01); *A61K 8/36* (2013.01); *A61K 8/361* (2013.01); *A61K 8/375* (2013.01); *A61K 8/39* (2013.01); *A61K 8/466* (2013.01); *A61K 8/731* (2013.01); *A61K 8/8152* (2013.01); *A61K 8/8158* (2013.01); *A61K 8/86* (2013.01); *A61K 8/88* (2013.01); *A61K 8/891* (2013.01); *A61K 8/90* (2013.01); *A61Q 1/02* (2013.01); *A61Q 1/04* (2013.01); *A61Q 19/00* (2013.01); *A61Q 19/001* (2013.01); *A61K 2800/5424* (2013.01)

(58) Field of Classification Search
None
See application file for complete search history.

(56) References Cited

U.S. PATENT DOCUMENTS

| | | | |
|---|---|---|---|
| 2008/0311066 A1 | 12/2008 | Samain et al. | |
| 2011/0110989 A1* | 5/2011 | Simonnet | A61K 8/8147 424/401 |
| 2014/0134255 A1 | 5/2014 | Saito et al. | |

FOREIGN PATENT DOCUMENTS

| | | |
|---|---|---|
| CN | 103191027 A | 7/2013 |
| CN | 105050574 A | 11/2015 |

(Continued)

OTHER PUBLICATIONS

English translation for JP 2012-241004A (Year: 2012).*

(Continued)

*Primary Examiner* — Sin J Lee
(74) *Attorney, Agent, or Firm* — Oblon, McClelland, Maier & Neustadt, L.L.P.

(57) ABSTRACT

A composition comprising at least one dispersed fatty phase, and at least one continuous aqueous phase, and comprising: a) at least one hydrophobic gelling agent selected from ester of dextrin and fatty acid; b) at least one amphiphilic cross-linked copolymer; c) at least one anionic terpolymer, linear or branched, of at least one monomer (1) carrying an acid function in free form, partially or totally salified by a nonionic monomer (2) selected from N,N-dimethylacrylamide and 2-hydroxyethyl acrylate, and at least one monomer (3) polyoxyethylenated alkyl acrylate of formula (III) wherein in formula (III): R1 represents a hydrogen atom, R represents a linear or branched $C_8$-$C_{16}$ alkyl radical, n is an integer ranging from 1 to 10; and d) at least one hydrophobic particles chosen from hydrophobic silicas, hydrophobic cellulose, starch, talc, silicone resin powders, hollow hemispherical silicone particles, polyamide powders, hydrophobic pigments, or a mixture thereof.

(III)

12 Claims, No Drawings

(56) References Cited

FOREIGN PATENT DOCUMENTS

| EP | 2 740 462 A1 | 6/2014 |
|---|---|---|
| JP | 7-138129 A | 5/1995 |
| JP | 8-283303 A | 10/1996 |
| JP | 2002-193740 A | 7/2002 |
| JP | 2011-511824 A | 4/2011 |
| JP | 2012-241004 A | 12/2012 |
| JP | 2013-227444 A | 11/2013 |
| KR | 10-2015-0121211 A | 10/2015 |
| WO | WO 2006/013270 A2 | 2/2006 |
| WO | WO 2009/101113 A2 | 8/2009 |
| WO | WO 2015/089716 A1 | 6/2015 |

OTHER PUBLICATIONS

English translation for JP 08-283303A (Year: 1996).*
Partial English translation for JP 2012-241004A (for Example 6), provided by Google translation (Year: 2012).*
Sakazaki ("Particles with tunable wettability for solid-stabilized emulsions", Journal of Dispersion Science and Technology, vol. 40(2), p. 219-230 (2019)). (Year: 2019).*
Yang et al ("An Overview of Pickering Emulsions: Solid-Particle Materials, Classification, Morphology, and Applications" Frontiers in Pharmacology (published on Mary 23, 2017) (Year: 2017).*
A webpage article obtained from: https://cosmetics.specialchem.com/inci-ingredients/dextrin-myristate (date unknown).*
Korean Office Action dated Aug. 26, 2020 in Korean Patent Application No. 10-2019-7003183 (with English language translation), 10 pages.
Extended European Search Report dated Feb. 13, 2020 in European Patent Application No. 16908423.3, 7 pages.
International Search Report and Written Opinion dated Mar. 10, 2017 in PCT/CN2016/089788 filed on Jul. 12, 2016.
Japanese Office Action dated Jan. 6, 2020, in Patent Application No. 2019-500832, 9 pages (with English translation).
Combined Chinese Office Action and Search Report dated Jun. 3, 2021 in Patent Application No. 201680087619.8 (with English translation of Category of Cited Documents), 9 pages.

* cited by examiner

COMPOSITION OF PICKERING EMULSION

TECHNICAL FIELD

The present invention relates to the field of cosmetics, and especially to the field of compositions in the form of visible oil droplets suspending in an aqueous phase.

BACKGROUND ART

Two-phase compositions which appeal to consumers on account of their aesthetic nature exist currently on the market. These compositions consist of two mutually immiscible phases, either are comprised of fatty phase dispersing in an aqueous phase in form of oil droplets, or are mixed together extemporaneously by shaking before use.

Pickering emulsion, due to its aesthetic nature and surfactant-free property, is of great interest of the consumers and widely used in the cosmetic products. To form a Pickering emulsion, finely divided solid particles are adsorbed at the interface between the oil and the homogeneous mixture, and serve to stabilize the oil droplets.

However, these emulsions have a tendency to become destabilized on storage over time. The sedimentation of the solid particles or even phase separation is observed, leading to an appearance that consumers find unappealing. In order to improve the stability, FR1160798 disclosed a Pickering emulsion comprising apolar hydrocarbon-based oil, $C_1$-$C_4$ monoalcohol, and hydrophobic silica aerogel particles. However, due to the existing of a relatively high amount of alcohol, which is necessary for improving the stability of the Pickering emulsion, a discomfort after application of the emulsion is observed by the consumers.

Efforts have been made to formulate a Pickering emulsion, which is stable over time, with low amount of alcohol.

However, the stability is still to be improved during scaling up process, during which a product undergoes shearing forces at least once, In particular, the stability is to be improved during scaling up, for example at a high quantity, such as greater than or equal to 40 kg.

The inventors found it difficult to formulate a Pickering emulsion with an improved scaling up stability by simply increasing the viscosity of the fatty phase and/or aqueous phase. In some cases, visible oil droplets are not formed; in other cases, oil droplets do not appear to be circular shapes as expected, due to the change of viscosity. Moreover, the oil droplets coalescent during and immediately after scaling up process, this is not expected.

There is thus a need for developing a composition of Pickering emulsion type, wherein the oil droplets are visible, and that has improved scaling up stability.

Meanwhile, such a composition maintains good stabilities such as stability under different temperatures, during two months.

There is also a need for formulating a composition with above mentioned property, and having a good aesthetic nature, in particular, the oil droplets are in form of globules or circular shape.

Additionally, such a composition also has a good stability during routine use by the consumers. The appearance of the mutually immiscible phases remains as expected after shaking.

Moreover, there is a need for formulating a composition with above mentioned properties, and meanwhile having a good sensory after application.

DISCLOSURE OF INVENTION

It is discovered that, in accordance to the present invention, a composition comprising a dispersed fatty phase and a continuous aqueous phase, and comprising hydrophobic gelling agent(s), amphiphilic crosslinked polymer(s), anionic terpolymer(s), and hydrophobic particles solves the problems mentioned above.

Thus, a subject of the present invention is a composition comprising at least one dispersed fatty phase, and at least one continuous aqueous phase, and comprising:

a) at least one hydrophobic gelling agent selected from ester of dextrin and fatty acid;

b) at least one amphiphilic crosslinked copolymer;

c) at least one anionic terpolymer, linear or branched, of at least one monomer (1) carrying an acid function in free form, partially or totally salified by a nonionic monomer (2) selected from N,N-dimethylacrylamide and 2-hydroxyethyl acrylamide, and at least one monomer (3) polyoxethylenated alkyl acrylate of formula (III)

formula (III)

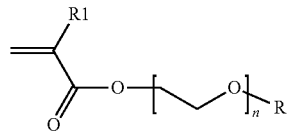

wherein in formula (III):

R1 represents a hydrogen atom,

R represents a linear or branched $C_2$-$C_8$ radical, n is an integer ranging from 1 to 10; and d) at least one hydrophobic particles chosen from hydrophobic silicas, hydrophobic cellulose, starch, talc, silicone resin powders, hollow hemispherical silicone particles, polyamide powders, hydrophobic pigments, or a mixture thereof.

The other subject of the present invention is a cosmetic process for making up and/or caring for the keratin materials, for example the skin, in particular the face and the lips, by applying to the keratin materials the composition of the present invention.

The term "Pickering emulsion" refers to an emulsion that is stabilized by solid particles (for example colloidal silica) which adsorb onto the interface between the two phases.

The term "keratin material" means the skin (of the body, face and around the eyes), hair, eyelashes, eyebrows, bodily hair, nails, lips or mucous membranes.

The term "visible oil droplets" of the present invention refers to the oil droplets with a mean diameter ranging from 0.01 mm to 10 mm. The oil droplets are visible by observing them using the bear eyes.

The mean diameter of the oil droplets of the present invention is measured using 64-bit "Image-Pro Premier 9.1" analysis software sold by the company MEDIA.

A composition of the present invention is placed in an evaporating dish, and an image of the composition is captured by a Macro-lens camera. The image is then analyzed by the "Image-Pro Premier 9.1" analysis software. Finally the mean diameter of the oil droplets is calculated according to the pixel data obtained from the software.

The term "scaling up stability" means a composition according to the present invention that forms visible circular oil droplets without coalescence at the production of at least 40 kg, and that does not undergo any significant change in its structure or properties for at least one month after its manufacture and especially for at least two months after its manufacture in a large quantity, such as greater than or equal to 40 kg.

The term "scaling up" is intended to mean the process from preparing a composition according to the invention to the filling of the composition is completed. In particular, during the process, there exist at least two steps wherein the composition undergoes shearing force.

DETAILED DESCRIPTION OF THE INVENTION

Fatty Phase

According to the present invention, the composition comprises at least one dispersed fatty phase.

In particular, the fatty phase of the present invention is in form of droplets.

More particularly, the droplets have a mean diameter from 0.01 mm to 10 mm, preferably from 0.1 mm to 5 mm.

Preferably, the composition comprises a fatty phase presenting in an amount ranging from 0.1% to 40% by weight, preferably from 0.5% to 30% by weight, and more preferably from 1% to 20% by weight relative to the total weight of the composition.

Oils

A composition in accordance with the present invention comprises a dispersed fatty phase, wherein it comprises at least one oil.

The oil is selected from silicone oils, hydrocarbon-based oils, or a mixture thereof.

The term "silicone oil" is intended to mean an oil comprising at least one silicone atom, and in particular comprising Si—O group.

The term "hydrocarbon-based oil" (or "hydrocarbonated oil", or "hydrocarbon oil") means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The oil can be volatile or non-volatile.

The term "volatile" means an oil that is capable of evaporating on contact with keratin materials in less than one hour, at room temperature (25° C.) and atmospheric pressure (760 mmHg). The volatile oil is a volatile cosmetic oil, which is liquid at room temperature, especially having a non-zero vapour pressure, at room temperature and atmospheric pressure, in particular having a vapour pressure ranging from 0.13 Pa to 40000 Pa (10-3 to 300 mmHg), preferably ranging from 1.3 Pa to 13000 Pa (0.01 to 100 mmHg) and preferentially ranging from 1.3 Pa to 1300 Pa (0.1 to 10 mmHg).

The term "non volatile" means an oil whose vapour pressure at room temperature and atmospheric pressure is non-zero and less than 0.02 mmHg (2.66 Pa) and better still less than 10-3 mmHg (0.13 Pa).

According to an embodiment, the composition of the present invention comprises at least one non volatile hydrocarbonated plant oils.

Mentions can be made of the non volatile hydrocarbonated plant oil such as liquid triglycerides of fatty acids containing from 4 to 10 carbon atoms, for instance heptanoic or octanoic acid triglycerides, jojoba oil, or caprylic and/or capric acid triglycerides, for example the one sold under the tradename Myritol® 318 by the company Cognis (BASF);

According to an embodiment, the composition of the present invention comprises from 0.1% to 40% by weight, preferably from 0.5% to 30% by weight, and more preferably from 1% to 20% by weight of at least one oil, relative to the total weight of the composition.

Aqueous Phase

The composition according to the invention comprises a continuous aqueous phase.

The continuous aqueous phase comprises water.

The continuous aqueous phase may also comprise water-miscible organic solvents (at room temperature of 20-25° C.), for instance polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

Furthermore, the aqueous phase may also comprise cosmetically acceptable additives such as stabilizers, pH adjusters, or a mixture thereof.

In particular, a composition of the invention may comprise an aqueous phase in an amount ranging from 55% to 99.9% by weight, especially from 60% to 90% and more particularly from 65% to 85% by weight relative to the total weight of the composition.

Hydrophobic Gelling Agent(s)

According to the invention, the composition comprises at least one hydrophobic gelling agent selected from ester of dextrin and a fatty acid, saturated or unsaturated, linear or branched, preferably a $C_{12}$ to $C_{24}$ fatty acid.

Preferably, the dextrin ester is an ester of dextrine and a $C_{14}$-$C_{18}$ fatty acid.

More preferably, the dextrin ester is Dextrin Myristate, for example such as those commercialized under the references Rheopearl MKL2® by the company CHIBA FLOUR.

Preferably a composition according to the invention may comprise a content of dextrin ester ranging from 0.01% to 10% by weight and preferably from 0.05% to 5% by weight, relative to the total weight of the composition.

Amphiphilic Crosslinked Copolymer(s)

The composition of the present invention comprises at least one amphiphilic crosslinked copolymer.

Preferably, the amphiphilic crosslinked copolymer comprises at least one unit of an unsaturated olefinic carboxylic acid, and at least one hydrophobic unit of a ($C_{10}$-$C_{30}$)alkyl ester of unsaturated carboxylic acid.

In particular, the unsaturated olefinic carboxylic acid unit is a hydrophilic unit.

In particular, the ($C_{10}$-$C_{30}$)alkyl ester of unsaturated carboxylic acid unit is a hydrophobic unit.

Thus, such crosslinked copolymer may comprise at least one hydrophilic unit of the olefinic unsaturated carboxylic acid type and at least one hydrophobic unit of ($C_{10}$-$C_{30}$)alkyl ester of unsaturated carboxylic acid type. As used herein, "at least one crosslinked copolymer" means one crosslinked copolymer or a mixture of copolymers.

In one embodiment, said copolymer is a block copolymer.

As used herein, the term ($C_{10}$-$C_{30}$)alkyl means an alkyl group, linear or branched, comprising from 10 to 30 carbon atoms.

In one embodiment, the molecular weight of the above-mentioned copolymer is of at least 50 kD.

In one embodiment, the above-mentioned crosslinked copolymer is chosen from those comprising:

at least one unit derived from olefinic unsaturated carboxylic acid monomers of formula (I):

$$H_2C=C(R_1)-C(=O)-OH \quad (I)$$

wherein $R_1$ is selected from the group consisting of: H, $CH_3$, and $C_2H_5$, (which corresponds respectively to acrylic acid, methacrylic acid and ethacrylic acid units), and at least one unit derived from $(C_{10}-C_{30})$alkyl esters of unsaturated carboxylic acid monomers of formula (II):

$$H_2C=C(R_2)-COR_3(=O) \quad (II)$$

wherein $R_2$ is selected from the group consisting of: H, $CH_3$, and $C_2H_5$ (which corresponds respectively to acrylate, methacrylate and ethacrylate units), and $R_3$ is a saturated or unsaturated, branched or unbranched $(C_{10}-C_{30})$alkyl group.

As used herein, the term "at least one unit derived from olefinic unsaturated carboxylic acid monomers of formula (I)" means that said unit is formed from the monomers of formula (I), for example by polymerization of the monomers of formula (I).

In one embodiment, for example, $R_2$ is chosen from H (acrylate units) and $CH_3$ (methacrylate units) and $R_3$ is chosen from $(C_{12}-C_{22})$alkyl groups.

$(C_{10}-C_{30})$alkyl esters of unsaturated carboxylic acids in accordance with the invention include for example lauryl acrylate, stearyl acrylate, decyl acrylate, isodecyl acrylate, dodecyl acrylate, lauryl methacrylate, stearyl methacrylate, decyl methacrylate, isodecyl methacrylate, and dodecyl methacrylate.

Crosslinked copolymer of this type are for example described and prepared according to U.S. Pat. Nos. 3,915, 921 and 4,509,949, the disclosures of which are incorporated by reference herein.

In one embodiment, the crosslinked copolymer that can be used include those formed from a mixture of monomers comprising:
(a) acrylic acid,
(b) at least one ester of formula (II) described above wherein $R_2$ is chosen from H and $CH_3$, and $R_3$ is chosen from alkyl groups comprising from 12 to 22 carbon atoms, and
(c) at least one crosslinking agent chosen from copolymerizable polyethylenic unsaturated monomers such as diallyl phthalate, allyl (meth)acrylate, divinylbenzene, (poly)ethylene glycol dimethacrylate and methylenebisacrylamide.

In one embodiment, the crosslinked copolymers of the invention that can be used include (% being given with respect to the total weight of the respective copolymers):
copolymers comprising from 95% to 60% by weight of acrylic acid (hydrophilic unit), from 4% to 40% by weight of $C_{10}-C_{30}$ alkyl acrylate (hydrophobic unit), and from 0% to 6% by weight of crosslinking polymerizable monomer, and
copolymers comprising from 98% to 96% by weight of acrylic acid (hydrophilic unit), from 1% to 4% by weight of $C_{10}-C_{30}$ alkyl acrylate (hydrophobic unit) and from 0.1% to 0.6% by weight of crosslinking polymerizable monomer such as those described above.

Among the above crosslinked copolymers, the products sold by the company Lubrizol under the trade names PEMULEN TR1®, PEMULEN TR2®, and CARBOPOL 1382® can be used.

Preferably, the crosslinked copolymer used in the present invention is PEMULEN TR2®, which is an acrylates/$C_{10}$-$C_{30}$ alkyl acrylate crosspolymer.

Preferably, the amphiphilic crosslinked copolymer is present in the composition of the present invention ranging from 0.001% to 5% by weight, preferably from 0.005% to 2% by weight, relative to the total weight of the composition.

Anionic Terpolymer(s)

The composition of the present invention comprises at least one anionic terpolymer, linear or branched, of at least one monomer (1) carrying an acid function in free form, partially or totally salified by a nonionic monomer (2) selected from N,N-dimethylacrylamide and 2-hydroxyethyl acrylate, and at least one monomer (3) polyoxethylenated alkyl acrylate of formula (III)

formula (III)

$$\text{structure with } R1, \text{ ester group, } -O-(CH_2CH_2O)_n-R \quad (III)$$

wherein in formula (III):
R1 represents a hydrogen atom,
R represents a linear or branched $C_8$-$C_{16}$ alkyl radical;
n is an integer ranging from 1 to 10.

Preferably, the acid function of the monomer (1) is selected from sulfonic acid function, or phosphonic acid. Said function is in free form, partially or totally salified.

The monomer (1) may be selected from styrene sulfonic acid, ethylsulfonic acid or 2-methyl-2-[(1-oxo-2-propenyl]amino]-1-propanesulfonic acid (also known Acryloyldimethyltaurate) in free form, partially or totally salified. It is present in the anionic terpolymer of the invention preferably in molar proportion between 5 and 95% molar and more particularly between 10 and 90 mol %.

The monomer (1) will be more particularly 2-methyl-2-[(1-oxo-2-propenyl]amino]-1-propanesulfonic acid in free form, partially or totally salified.

The acid form function partially or completely salified is preferably an alkali metal salt such as sodium or potassium salt, an ammonium salt, an amino alcohol as a monoethanolamine salt or a salt of amino acid such as lysine salt.

The monomer (2) is preferably present in the anionic terpolymer of invention in the molar proportions of between 4.9 and 90 mol % and more particularly between 9.5 and 85 mol % and more particularly between 19.5 and 75 mol %.

Examples of linear $C_8$-$C_{16}$ alkyl radical in the formula (III) include octyl radical, decyl radical, undecyl radical, tridecyl radical, tetradecyl radical, pentadecyl radical, or hexadecyl radical.

Examples of branched $C_8$-$C_{16}$ alkyl radical in the formula (III), there may be mentioned are 2-ethylhexyl, 2-propylheptyl, 2-butyloctyl, 2-pentylnonyl, 2-hexyldecyl, 4-methylpentyl, 5-methylhexyl, 6-methylheptyl, 15-methylpentadecyl, 16-methylheptadecyl, or 2-hexyloctyl radical.

In a particular preferred embodiment of the invention, in the formula (III), R denotes a linear or branched $C_{12}$-$C_{16}$ alkyl radical.

In a particular embodiment of the invention, in the formula (III), n represents an integer from 3 to 5.

More particularly, the monomer used in the formula (III) is tetra ethoxylated lauryl acrylate.

The monomer (3) of the formula (III) is preferably present in the anionic terpolymer of invention in the molar proportions of between 0.1 and 10 mol % and more particularly between 0.5 and 5 mol %.

According to a particular embodiment of the invention, the anionic terpolymer is crosslinked and/or connected by a diethylenic or polyethylenic compound in the proportion, expressed relative to the total amount of monomers employed, of 0.005 to 1 mol % and preferably from 0.01 to 0.5 mol % and more particularly from 0.01 to 0.25 mol %.

The crosslinking agent and/or the branching agent is preferably selected from Ethylene glycol dimethacrylate, the diallyloxoacétique acid or a salt thereof such as sodium diallyloxyacetate, tetraallyloxyethane, ethylene glycol diacrylate, Ure diallyl amine, triallyl trimethylolpropane triacrylate, the methylenebis (acrylamide) or mixtures thereof.

The anionic terpolymer of the present invention may contain additives such as complexing agents, transfer agents, chain-limiting agents.

More particularly, the anionic terpolymer can be used in the present invention is 2-methyl-2-[(1-oxo-2-propenyl] amino]-1-propanesulfonic acid, partially or totally salified in the form of ammonium salt, of N, N-dimethylacrylamide and lauryl acrylate and crosslinked with trimethylol tetraethoxylated propanetriacrylate under the INCI name: Polyacrylate Crosspolymer-6, such as the product sold under the trade name SEPIMAX ZEN® by Seppic.

Preferably, the anionic terpolymer is present in the composition of the present invention in an amount ranging from 0.0005% to 5% by weight, preferably from 0.001% to 3% by weight, relative to the total weight of the composition.

Hydrophobic Particles

A composition according to the present invention comprises at least one hydrophobic particle.

For the purpose of the invention, these particles adsorb onto the interface between the fatty phase and aqueous phase, so as to stabilize the emulsion.

Moreover, these particles enables the oil droplets of the present invention, which are visible, to be dispersed into the aqueous phase in a long-term, for example for one month, or for example for two months.

The particles may be mineral or organic, and may be in form of spherical particles, or lamellar particles.

In the present patent application, the term "spherical particles" means particles in the form or substantially in the form of a sphere, which are insoluble in the medium of the composition according to the invention, even at the melting point of the medium (about 100° C.).

The term "lamellar particles" means herein particles of parallelepipedal shape (rectangular or square surface), discoid shape (circular surface) or ellipsoid shape (oval surface), characterized by three dimensions: a length, a width and a height, these particles being insoluble in the medium of the composition according to the invention, even at the melting point of the medium (about 100° C.).

More particularly, the hydrophobic particles are chosen from:

hydrophobic silica,

The term "hydrophobic silica" is understood to mean, in the context of the present invention, both pure hydrophobic silicas and particles coated with hydrophobic silica.

According to a specific embodiment, the hydrophobic silicas which can be used in the composition of the invention are amorphous and of fumed origin. They are preferably provided in the pulverulent form.

The amorphous hydrophobic silicas of fumed origin are obtained from hydrophilic silicas. The latter are obtained by pyrolysis of silicon tetrachloride ($SiCl_4$) in a continuous flame at 1000° C. in the presence of hydrogen and oxygen. They are subsequently rendered hydrophobic by treatment with halogenated silanes, alkoxysilanes or silazanes. The hydrophobic silicas differ from the starting hydrophilic silicas, inter alia, in a lower density of silanol groups and in a smaller adsorption of water vapour.

According to this embodiment, the hydrophobic silica is preferably chosen from silicas having a specific surface of from 50 to 500 $m^2/g$ and a number-average particle size ranging from 3 to 50 nm. These are more particularly the hydrophobic silicas described in the following table, and their mixtures.

|  | Commercial name | | | | |
| --- | --- | --- | --- | --- | --- |
|  | Aerosil R202 (Evonik Degussa) | Aerosil R805 (Evonik Degussa) | Aerosil R812 (Evonik Degussa) | Aerosil R972 (Evonik Degussa) | Aerosil R974 (Evonik Degussa) |
| BET surface ($m^2/g$) | 90 + 20 | 150 + 25 | 260 + 30 | 110 + 20 | 170 + 20 |
| Average particle size (nm) | 14 | 12 | 7 | 1 | 12 |

According to this embodiment, the hydrophobic silica used in the composition of the invention can also consist of a particle completely or partially covered with silica, in particular of an inorganic particle completely or partially covered with hydrophobic silica, such as pigments and metal oxides covered with hydrophobic silica. These particles can also have optical properties in the product and on the skin; for example, they can have a mattifying or slightly whitening effect.

Use is preferably made, as hydrophobic silica, of a hydrophobic fumed silica treated at the surface with a dimethylsiloxane, such as that sold under the name Aerosil R972 (INCI name: Silica Dimethyl Silylate) by Evonik Degussa.

According to another specific embodiment, the hydrophobic silica which can be used in the composition of the invention are aerogel particles of hydrophobic silica exhibiting a specific surface per unit of weight (SW) ranging from 500 to 1500 $m^2/g$ and a size, expressed as volume-average diameter (D[0.5], also known as median particle size by volume Dv50), ranging from 1 to 1500 μm.

Silica aerogels are porous materials obtained by replacing (by drying) the liquid component of a silica gel with air.

They are generally synthesized via a sol-gel process in a liquid medium and then dried, usually by extraction of a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science: New York: Academic Press, 1990.

The aerogel particles of hydrophobic silica used in the present invention exhibit a specific surface per unit of weight (SW) ranging from 500 to 1500 m$^2$/g, preferably from 600 to 1200 m$^2$/g and better still from 600 to 800 m$^2$/g, and a size, expressed as volume-average diameter (D[0.5], also known as median particle size by volume Dv50), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the aerogel particles of hydrophobic silica used in the present invention exhibit a size, expressed as volume-average diameter (D[0.5], also known as median particle size by volume Dv50), ranging from 1 to 30 μm, preferably from 5 to 25 μm, better still from 5 to 20 μm and even better still from 5 to 15 μm.

The specific surface per unit of weight can be determined by the nitrogen absorption method, known as the BET (Brunauer-Emmett-Teller) method, described in The Journal of the American Chemical Society, Vol. 60, page 309, February 1938, and corresponding to the international standard ISO 5794/1 (appendix D). The BET specific surface corresponds to the total specific surface of the particles under consideration. The sizes of the aerogel silica particles can be measured by static light scattering using a commercial particle size analyser of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, N.Y., 1957.

According to an advantageous embodiment, the aerogel particles of hydrophobic silica used in the present invention exhibit a specific surface per unit of weight (SW) ranging from 600 to 800 m$^2$/g and a size, expressed as volume-average diameter (D[0.5], also known as median particle size by volume Dv50), ranging from 5 to 20 μm and even better still from 5 to 15 μm.

The aerogel silica particles used in the present invention can advantageously exhibit a packed density (p) ranging from 0.04 g/cm3 to 0.10 g/cm3 and preferably from 0.05 g/cm3 to 0.08 g/cm3.

In the context of the present invention, this density, known as the packed density, can be assessed according to the following protocol:

40 g of powder are poured into a graduated measuring cylinder; the measuring cylinder is then placed on the Stay 2003 device from Stampf Volumeter; the measuring cylinder is subsequently subjected to a series of 2500 packing actions (this operation is repeated until the difference in volume between two consecutive tests is less than 2%); the final volume Vf of packed powder is then measured directly on the measuring cylinder. The packed density is determined by the ratio w/Vf, in the case in point 40/Vf (Vf being expressed in cm$^3$ and w in g).

According to one embodiment, the aerogel particles of hydrophobic silica used in the present invention exhibit a specific surface per unit of volume SV ranging from 5 to 60 m$^2$/cm$^3$, preferably from 10 to 50 m$^2$/cm$^3$ and better still from 15 to 40 m$^2$/cm$^3$.

The specific surface per unit of volume is given by the relationship: SV=SW×ρ where ρ is the packed density, expressed in g/cm$^3$, and SW is the specific surface per unit of weight, expressed in m$^2$/g, as defined above.

Preferably, the aerogel particles of hydrophobic silica according to the invention have an oil absorption capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method for determining the oil uptake of a powder described in Standard NF T 30-022. It corresponds to the amount of oil adsorbed onto the available surface of the powder and/or absorbed by the powder by measurement of the wet point, described below:

An amount w=2 g of powder is placed on a glass plate, and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread on the glass plate without cracking or forming lumps. The volume Vs (expressed in ml) of oil used is then noted.

The oil uptake corresponds to the ratio Vs/w.

The aerogels used according to the present invention are hydrophobic silica aerogels, preferably of silylated silica (INCI name: silica silylate).

The term "hydrophobic silica" is understood to mean any silica whose surface is treated with silylating agents, for example with halogenated silanes, such as alkylchlorosilanes, siloxanes, in particular dimethylsiloxanes, such as hexamethyldisiloxane, or silazanes, so as to functionalize the OH groups with silyl groups Si—Rn, for example trimethylsilyl groups.

As regards the preparation of aerogel particles of hydrophobic silica modified at the surface by silylation, reference may be made to the document U.S. Pat. No. 7,470,725.

Use will in particular be made of aerogel particles of hydrophobic silica modified at the surface with trimethylsilyl groups (trimethylsiloxylated silica).

Mention may be made, as hydrophobic silica aerogels which can be used in the invention, for example, of the aerogel sold under the name VM-2260 (INCI name: Silica silylate) by Dow Corning, the particles of which exhibit an average size of approximately 1000 microns and a specific surface per unit of weight ranging from 600 to 800 m$^2$/g.

Mention may also be made of the aerogels sold by Cabot under the references Aerogel TLD 201, Aerogel OGD 201 and Aerogel TLD 203.

Use will more particularly be made of the aerogel sold under the name VM-2270 (INCI name: Silica silylate) by Dow Corning, the particles of which exhibit an average size ranging from 5 to 15 microns and a specific surface per unit of weight ranging from 600 to 800 m$^2$/g.

hydrophobic cellulose, for example alkyl cellulose; mentions may be made of the product ethyl cellulose sold under the trade name Ethocel™ Standard 200 Industrial Ethylcellulose from Dow Chemicals,
  starches, All the starches and flours are suitable for use herein and may be derived from any native source. Preferably mention may be made of hydrophobic or hydrophobically modified starches. Also suitable are starches and flours derived from a plant obtained by standard breeding techniques including crossbreeding, translocation, inversion, transformation or any other method of gene or chromosome engineering to include variations thereof. In addition, starch or flours derived from a plant grown from artificial mutations and variations of the above generic composition which may be produced by known standard methods of mutation breeding are also suitable herein. Typical sources for the starches and flours are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof.

In particular, hydrophobically modified starches according to the present invention are preferred. Such starches include, for example, aluminum starch octenylsuccinate. Aluminum starch octenylsuccinate is commonly sold under the tradename DRY-FLO PURE by the company Akzo Nobel.

The starch may be first nonionically derivatized using an ester or ether which is compatible with the system, particularly with the solvent. Methods of nonionically derivatization are well known in the art and may be found for example in Starch Chemistry and Technology, 2nd ed., Edited by Whistler, et al., Academic Press, Inc., Orlando (1984) or Modified Starches: Properties and Uses. Wurzburg, O. B., CRC Press, Inc., Florida, (1986).

Nonionic reagents include, but are not limited to alkylene oxides such as ethylene oxide, propylene oxide, and butylene oxide, acetic anhydride, and butyl ketene dimer. Particularly suitable nonionic reagents are the alkylene oxides, more particularly propylene oxide.

Typically, the modified starches are powders at room temperature and atmospheric pressure. The modified starch powders are fine-grained. Further, the modified starch of the present invention has a particle size distribution of 5-30 microns and an average particle size of 15 microns. Moreover, the refractive index of the modified starch is measured to be between 1.50 and 1.60 at 25° C., preferably 1.52.

talc

The hydrophobic particle may be chosen from talc.

More particularly, the talc is micro-talc (for instance Micro Ace P3 by Nippon Talc.

Micro-talc particle sizes preferably range from 1 to 300 μm; most preferably ranging from 2 to 15 μm. The talc particles may be used alone or in combination. Hybrid powders may be employed, including talc in combination with titanium dioxide, aluminum oxide, and silicon (for instance Coverleaf AR80 from Presperse LLC), talc in combination with aluminum oxide and silicone dioxide (for instance Coverleaf AR100).

Other hybrid powder contemplated include zinc oxide on mica-barium sulfate (for instance Shadeleaf A from Merck), titanium dioxide on mica (for instance Blancsealer from Merck), titanium dioxide on silica (for instance NL T30H2WA from Nippon Sheet Glass), and titanium dioxide on mica-barium sulfate (for instance Naturaleaf powder from Merck).

Micro-talc is preferred in accordance to the present invention.

Silicone resin powders,

The preferred silicone resin powder is, for instance the silicone resin with the INCI name polymethylsilsesquioxane sold under the trade name Tospearl 145A by the company GE Silicone, with a mean size of 4.5 microns.

hollow hemispherical silicone particles, for instance methylsilanol/silicate crosspolymer sold under the trade name NLK 500, NLK 506 and NLK 510 by the company Takemoto Oil and Fat, polyamide (Nylon®) powders, for instance Nylon 12 particles of the SP-500 from Toray Industries, hydrophobic pigments, The hydrophobic pigments of the present invention may be hydrophobic or hydrophobic coated pigments. The hydrophobic coated pigments present in the emulsion according to the invention are pigments which are surface-treated with a hydrophobic agent. These treated pigments are well dispersed in the fatty phase.

As hydrophobic pigments, it is possible to use metal oxides such as iron oxides (in particular those which are yellow, red, brown or black in colour), titanium dioxides, cerium oxide, zirconium oxide, chromium oxide; manganese violet, ultramarine blue, Prussian blue, ferric blue, bismuth oxychloride, pearl, mica coated with titanium dioxide or with bismuth oxychloride, coloured pearlescent pigments such as mica-titanium with iron oxides, mica-titanium with in particular ferric blue or chromium oxide, mica-titanium with an organic pigment of the abovementioned type and pearlescent pigments based on bismuth oxychloride, and mixtures thereof.

Hydrophobic pigments of iron oxides or of titanium dioxide are preferably used.

The hydrophobic treatment agent may be chosen from silicones such as methicones, dimethicones, perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, amino acids; N-acylated amino acids or their salts; lecithin, isopropyl triisostearyl titanate, and mixtures thereof.

Preferably, fatty acids such as stearic acid is used as the hydrophobic treatment agent.

Mentions may be made of the hydrophobic coated pigment, such as metal oxides coated with fatty acids, for example titanium dioxide and aluminum hydroxide coated with stearic acid, which is sold under the tradename Micro Titanium Dioxide MT-100 T V by the company Tayca.

or a mixture thereof.

According to a preferred embodiment, the hydrophobic particles of the present invention are chosen from hydrophobic silica.

More preferably, the composition of the present invention comprises hydrophobic particles chosen from hydrophobic fumed silica treated at the surface with a dimethylsiloxane, aerogel particles of hydrophobic silica exhibiting a specific surface per unit of weight (SW) ranging from 500 to 1500 $m^2/g$ and a size, expressed as volume-average diameter (D[0.5], also known as median particle size by volume Dv50), ranging from 1 to 1500 μm, or a mixture thereof.

Even more preferably, the composition of the present invention comprises at least one hydrophobic particle chosen from silica dimethyl silylate, silica silylate, or a mixture thereof.

Preferably, the composition of the present invention comprises from 0.001% to 5% by weight, preferably from 0.02% to 2% by weight of the hydrophobic particles, relative to the total weight of the composition.

Additives

Preferably, a composition according to the invention further comprises at least one additive, chosen from hydrophilic solvents, lipophilic solvents, additional oils, or mixtures thereof.

The composition according to the invention may also comprise any additive usually used in the field under consideration, chosen, for example, from fillers or viscosity increasing agents, gelling agents, additional gums, resins, additional thickening agents, structuring agents such as waxes, dispersants, antioxidants, essential oils, preserving agents, fragrances, neutralizers, antiseptics, additional UV-screening agents, cosmetic active agents, such as vitamins, moisturizers, emollients or collagen-protecting agents, and mixtures thereof.

It is a matter of routine operations for a person skilled in the art to adjust the nature and amount of the additives present in the compositions in accordance with the invention such that the desired cosmetic properties and stability properties thereof are not thereby affected.

Galenic Form

The composition according to the invention is in form of an oil-in-water emulsion.

In particular, according to an embodiment, the composition of the present invention is in form of an oil-in-water Pickering emulsion.

More particularly, the composition of the present invention has a fatty phase in form of droplets, in particular visible oil droplets, with a mean diameter from 0.01 mm to 10 mm, preferably from 0.1 mm to 5 mm.

The mean diameter of the oil droplets of the present invention is measured using 64-bit "Image-Pro Premier 9.1" analysis software sold by the company MEDIA.

A composition is placed in an evaporating dish, and an image of the composition is captured by a Macro-lens camera. The image is then analyzed by the "Image-Pro Premier 9.1" analysis software. Finally the mean diameter of the oil droplets is calculated according to the pixel data obtained from the software.

More specifically, the mean diameter of the oil droplets is measured as following:

5-20 g of a composition according to the present invention is placed on an evaporating dish, at the bottom of which a bar with the length of 1 cm is marked. The 1 cm bar is used as a reference for measuring the mean diameter of oil droplets.

A photo of the dish containing the composition is taken using a macro-lens camera and is imported to the 64-bit Image-Pro Premier 9.1 analysis software, wherein the "cycle" module is applied in order to count the cycles of the oil droplets.

The software measures the 1 cm bar reference as well as the mean diameter of oil droplets, and presents both data in pixel.

Finally, the mean diameter is obtained by transforming the pixel into cm in comparison with the reference 1 cm bar.

The composition of the present invention may have the appearance of a cream, a gel, particularly a gel, an ointment, a milk, a lotion, a serum, a paste.

According to a preferred embodiment, the composition of the present invention is a gel, wherein the dispersed fatty phase is in form of visible oil droplets, preferably in globules or circular shape.

According to a preferred embodiment, the present invention relates to a composition comprising at least one dispersed fatty phase, and at least one continuous aqueous phase, and comprising:

a) from 0.05% to 5% by weight of at least one hydrophobic gelling agent selected from ester of dextrin and fatty acid;

b) from 0.005% to 2% by weight of at least one amphiphilic crosslinked copolymer;

c) from 0.001% to 3% by weight of at least one anionic terpolymer, linear or branched, of at least one monomer (1) carrying an acid function in free form, partially or totally salified by a nonionic monomer (2) selected from N,N-dimethylacrylamide and 2-hydroxyethyl acrylate, and at least one monomer (3) polyoxethylenated alkyl acrylate of formula (III)

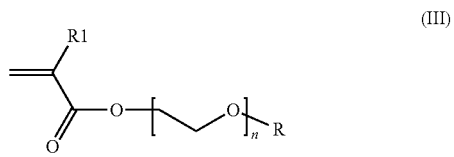

(III)

wherein in formula (III):
R1 represents a hydrogen atom,
R represents a linear or branched $C_8$-$C_{16}$ alkyl radical;
n is an integer ranging from 1 to 10; and
d) silica silylate.

Method and Use

The composition of the present invention can be used for a non-therapeutic process, such as a cosmetic process or method for caring for keratin materials, such as the skin, in particular the face and the lips, by being applied to the skin, especially the face and the lips.

The present invention also relates to a use of the composition according to the present invention, as it is or in cosmetic product for caring for the skin, especially for the face and the lips.

The examples that follow are aimed at illustrating the compositions and processes according to this invention, but are not in any way a limitation of the scope of the invention.

EXAMPLES

Example 1

Formulation Example

The following Pre-phases were prepared:

| Phase | INCI name | Pre-phase A according to the invention (% by weight by active) | Pre-phase B outside of the invention (% by weight by active) | Pre-phase C outside of the invention (% by weight by active) |
|---|---|---|---|---|
| A | SILICA SILYLATE (VM-2270 AEROGEL FINE PARTICLES from DOW CORNING) | 0.15 | 0.15 | 0.15 |
| | PROPYLENE GLYCOL | 3 | 3 | 3 |

-continued

| Phase | INCI name | Pre-phase A according to the invention (% by weight by active) | Pre-phase B outside of the invention (% by weight by active) | Pre-phase C outside of the invention (% by weight by active) |
|---|---|---|---|---|
| B | GELLAN GUM (KELCOGEL CG LA from CP KELCO) | 0 | 0.06 | 0 |
| | ACRYLATES/C10-30 ALKYL ACRYLATE CROSSPOLYMER (PEMULEN TR2 ® from LUBRIZOL) | 0.06 | 0 | 0.06 |
| | POLYACRYLATE CROSSPOLYMER-6 (SEPIMAX ZEN ® from SEPPIC) | 0.015 | 0.015 | 0 |
| | SODIUM HYDROXIDE | 0.001 | 0 | 0.001 |
| | CALCIUM CHLORIDE | 0 | 0,006 | 0 |
| | WATER | QS to 100 | QS to 100 | QS to 100 |
| C | CAPRYLIC/CAPRIC TRIGLYCERIDE (MYRITOL ® 318 from COGNIS (BASF)) | 15 | 15 | 15 |
| | DEXTRIN MYRISTATE (RHEOPEARL MKL2 from CHIBA FLOUR MILLING) | 2 | 2 | 2 |
| | COLORANT | 0.0001 | 0.0001 | 0.0001 |
| | Adjust pH | to 5.2 | to 5.6 | to 5.2 |

Remarks: Pre-phase B contains gellan gum instead of the amphiphilic crosslinked copolymer b) as claimed; Pre-phase C does not contain anionic terpolymer c) as claimed.

The Pre-phases listed above were prepared following the steps of:

phase B was swelled in water and pH was adjusted to 5.2, or 5.6, the mixture was then heated to 70° C.;

Phase A was dispersed in the mixture obtained above for 5 mins;

Phase C was melted at 85° C., and then introduced into the mixture obtained above for 2 mins until visible and circular oil droplets were observed;

The oil droplets obtained above were added to cooling water while stirring, the temperature was cooled to 30° C.

A base was prepared as following:

0.5% by weight of Carbomer (SYNTHALEN K from 3V) was swelled in water, then 0.15% of Sodium Hydroxide was added to the mixture, and pH was adjusted to 6.0 at 30° C.

Then, the final formulas of the present invention and comparative formulas were prepared:

| Phase | Invention formula A (% by weight by active) | Comparative formula B (% by weight by active) | Comparative formula C (% by weight by active) |
|---|---|---|---|
| Pre-phase A according to the invention | 25.0 | 0 | 0 |
| Pre-phase B outside of the invention | 0 | 25.0 | 0 |
| Pre-phase C outside of the invention | 0 | 0 | 25.0 |
| base | 75.0 | 75.0 | 75.0 | pre-phase was transferred from annex kettle to main kettle, and then mixed under stirring, until homogeneous;

The mixture was then dispatched from the kettle to storage. The production as mentioned above was conducted at a scale of 40 kg, wherein during transferring of the pre-phases, and dispatching of the final formulas, shearing force was applied to the pre-phases and the final formulas.

Example 2

Evaluation Example

The stability of the invention and comparative formulas prepared in the Example 1 were evaluated.

The stability tests of the invention formulas and the comparative formulas at 40° C., 45° C., and 65° C. for two months were conducted using Binder oven (USA), by leaving the invention and comparative formulas in the oven for 2 months.

The stability tests at 4° C. stability for two months were conducted using Zhongke Meiling refrigerator (YC-260L, China), by leaving the invention and comparative formulas in the refrigerator for 2 months.

The light stability tests for 24 hours were conducted using ATLAC (AMETEK Measurement and Calibration Technologies).

The freezing-thaw stability tests were conducted for 10 cycles using Binder over (USA). In each cycle, the temperature will be changed gradually from 20° C. to −20° C. in 24 hours.

The scaling up stability was conducted by investigating the appearance of the formulas during production process of 40 kg of the formulas as mentioned in the Example 1, such as the visibility of the beads, and the shape and size of the beads.

The result of the stability of the invention and comparative formulas were listed below.

| Test | | Invention formula A | Comparative formula B | Comparative formula C |
|---|---|---|---|---|
| Stability test at different temperatures in 2 months | 4° C. | OK | / | / |
| | 40° C. | OK | / | / |
| | 45° C. | OK | / | / |
| | 65° C. | OK | / | / |
| Light stability test | | OK | / | / |
| Freezing-shaw stability test | | OK | / | / |
| Scaling up stability of the Pre-phase or formula | | OK | Oil droplets coalescent in Pre-phase B, and no homogeneous oil droplets formed in Comparative formula B. | Partly coalescence of oil beads in Pre-phase C, gel with very ununiformed droplets in Comparative formula C |

It is observed the invention formula A is a composition containing visible and circular oil droplets, and present good stabilities under different conditions, whereas the comparative formula B does not contain oil droplets dispersing in the aqueous, as the oil droplets coalescent during the preparation of the Pre-phase B, and Comparative formula C does not contain circular and even oil droplets as expected. Part of the oil droplets in the Pre-phase C coalescent to each other, and thus form an ununiformed formula.

Besides, it is also observed by the consumers that, the invention formula A provides to the skin a good sensory during application, such as hydration, moisturizing.

It is also noted that during 2 months of routine use of the invention formula A by the consumers, it still possesses a good appearance, i.e., a gel with visible and circular oil droplets.

What is claimed is:

1. A composition comprising at least one dispersed fatty phase, and at least one continuous aqueous phase, and comprising:
   a) at least one hydrophobic gelling agent selected from ester of dextrin and saturated or unsaturated, linear or branched, $C_{12}$ to $C_{24}$ fatty acid;
   b) at least one amphiphilic crosslinked copolymer comprising at least one hydrophilic unit of an unsaturated olefinic carboxylic acid and at least one hydrophobic unit of a ($C_{10}$-$C_{30}$)alkyl ester of unsaturated carboxylic acid;
   c) at least one anionic terpolymer, linear or branched, of at least one monomer (1) carrying an acid function in free form, partially or totally salified by a nonionic monomer (2) selected from N,N-dimethylacrylamide or 2-hydroxyethyl acrylate, and at least one monomer (3) polyoxyethylenated alkyl acrylate of formula (III)

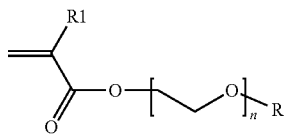

(III)

wherein in formula (III):
R1 represents a hydrogen atom,
R represents a linear or branched $C_8$-$C_{16}$ alkyl radical,
n is an integer ranging from 1 to 10; and
   d) at least one type of hydrophobic particles selected from the group consisting of hydrophobic silicas, hydrophobic cellulose, starch, talc, silicone resin powders, hollow hemispherical silicone particles, polyamide powders, hydrophobic pigments, and a mixture thereof,
wherein the composition is a surfactant-free pickering emulsion.

2. The composition of claim 1, wherein the at least one dispersed fatty phase is in form of a droplet with a mean diameter ranging from 0.01 mm to 10 mm.

3. The composition of claim 1, wherein the at least one dispersed fatty phase is present in an amount ranging from 0.1% to 40% by weight, relative to the total weight of the composition.

4. The composition of claim 1, wherein the at least one hydrophobic gelling agent is an ester of dextrin and a $C_{14}$-$C_{18}$ fatty acid.

5. The composition of claim 1, wherein the at least one hydrophobic gelling agent is present in an amount ranging 0.01% to 10% by weight, relative to the total weight of the composition.

6. The composition of claim 1, wherein the at least one amphiphilic crosslinked copolymer is present in an amount ranging from 0.001% to 5% by weight, relative to the total weight of the composition.

7. The composition of claim 1, wherein the at least one anionic terpolymer is present in the composition in an amount ranging from 0.0005% to 5% by weight, relative to the total weight of the composition.

8. The composition of claim 1, wherein the at least one type of hydrophobic particles is selected from the group consisting of silica dimethyl silylate, silica silylate, hydrophobic alkyl cellulose, aluminum starch octenylsuccinate, micro-talc, polymethylsilsesquioxane, methylsilanol/silicate crosspolymer, nylon-12, metal oxides, metal oxides coated with fatty acids, and a mixture thereof.

9. The composition of claim 1, wherein the at least one type of hydrophobic particle is present in an amount ranging from 0.001% to 5% by weight, relative to the total weight of the composition.

10. A process for making up and/or caring for keratin materials, comprising applying the composition according to claim 1 to the keratin materials.

11. A process for caring for and/or making up skin, comprising applying the composition according to claim 1 to the skin.

12. The composition of claim 1, wherein the at least one type of hydrophobic particles adsorb onto an interface between the at least one dispersed fatty phase and the at least one continous aqueous phase.

* * * * *

UNITED STATES PATENT AND TRADEMARK OFFICE
CERTIFICATE OF CORRECTION

| | |
|---|---|
| PATENT NO. | : 11,576,851 B2 |
| APPLICATION NO. | : 16/316068 |
| DATED | : February 14, 2023 |
| INVENTOR(S) | : Chen et al. |

It is certified that error appears in the above-identified patent and that said Letters Patent is hereby corrected as shown below:

On the Title Page

Column 2, Item (57), in "Abstract", Line 10, delete "polyoxethylenated" and insert
-- polyoxyethylenated --.

Signed and Sealed this
Eighth Day of August, 2023

Katherine Kelly Vidal
*Director of the United States Patent and Trademark Office*